United States Patent
Cohen

(10) Patent No.: US 12,000,070 B2
(45) Date of Patent: Jun. 4, 2024

(54) METHOD AND SYSTEM FOR LINE-BY-LINE ONE DIMENSIONAL FABRIC INSPECTION

(71) Applicant: USTER TECHNOLOGIES LTD., Caesarea (IL)

(72) Inventor: Shmuel Cohen, Kadima (IL)

(*) Notice: Subject to any disclaimer, the term of this patent is extended or adjusted under 35 U.S.C. 154(b) by 635 days.

(21) Appl. No.: 17/272,317

(22) PCT Filed: Aug. 21, 2019

(86) PCT No.: PCT/IB2019/057031
§ 371 (c)(1),
(2) Date: Feb. 28, 2021

(87) PCT Pub. No.: WO2020/044172
PCT Pub. Date: Mar. 5, 2020

(65) Prior Publication Data
US 2021/0238781 A1 Aug. 5, 2021

Related U.S. Application Data

(60) Provisional application No. 62/723,802, filed on Aug. 28, 2018.

(51) Int. Cl.
*G06T 7/90* (2017.01)
*D03J 1/00* (2006.01)
(Continued)

(52) U.S. Cl.
CPC .......... *D03J 1/007* (2013.01); *G01N 21/8851* (2013.01); *G06T 7/001* (2013.01);
(Continued)

(58) Field of Classification Search
CPC ............... D03J 1/007; G01N 21/8851; G01N 2021/8444; G01N 33/367; G06T 7/001;
(Continued)

(56) References Cited

U.S. PATENT DOCUMENTS 5,165,454 A * 11/1992 Kanayama ............ D03D 51/28
139/351
5,251,673 A 10/1993 Adachi et al.
2017/0029988 A1* 2/2017 Cohen ..................... D03J 1/007

FOREIGN PATENT DOCUMENTS

JP      H 5-186939 A      7/1993
WO      2006117673    *  11/2006
(Continued)

OTHER PUBLICATIONS

Neumann, F., Holtermann, T., Schneider, D., Kulczycki, A., Gries, T., & Aach, T. , "In-process fault detection for textile fabric production: onloom imaging" Optical Measurement Systems for Industrial Inspection VII, May 2011, pp. 1204-1215, vol. 8082,, SPIE, Bellingham, Washington USA.

*Primary Examiner* — Sheela C Chawan
(74) *Attorney, Agent, or Firm* — AlphaPatent Associates Ltd.; Daniel J. Swirsky

(57) ABSTRACT

System and method for on-loom fabric inspection includes an imaging device collecting images of a weaving area of a loom, a frame grabber receiving images of a fell-pick of and sending compact image data packages to an image processor. Irregularities may be detected by comparing a digital string representing the characteristic sequence of warp-risers and warp-sinkers along the fell-pick with a corresponding row (901) of required warp-risers and required warp-sinkers in a reference matrix (900) representing a required weaving pattern. The digital string may be a sequence of Boolean values.

21 Claims, 11 Drawing Sheets

(51) Int. Cl.
*G01N 21/88* (2006.01)
*G06T 7/00* (2017.01)
*H04N 23/60* (2023.01)
*G01N 21/84* (2006.01)

(52) U.S. Cl.
CPC .............. *G06T 7/90* (2017.01); *H04N 23/60* (2023.01); *G01N 2021/8444* (2013.01); *G06T 2207/10024* (2013.01); *G06T 2207/30124* (2013.01); *G06T 2207/30168* (2013.01)

(58) Field of Classification Search
CPC ............. G06T 7/90; G06T 2207/10024; G06T 2207/30124; G06T 2207/30168; G06T 7/0008; G06T 2207/10016; G06T 2207/10028; H04N 23/60; D06H 3/125; D03D 51/18
USPC .................................................. 382/111, 100
See application file for complete search history.

(56) References Cited

FOREIGN PATENT DOCUMENTS

WO 2006117673 A1 11/2006
WO 2019106509 A1 6/2019

* cited by examiner

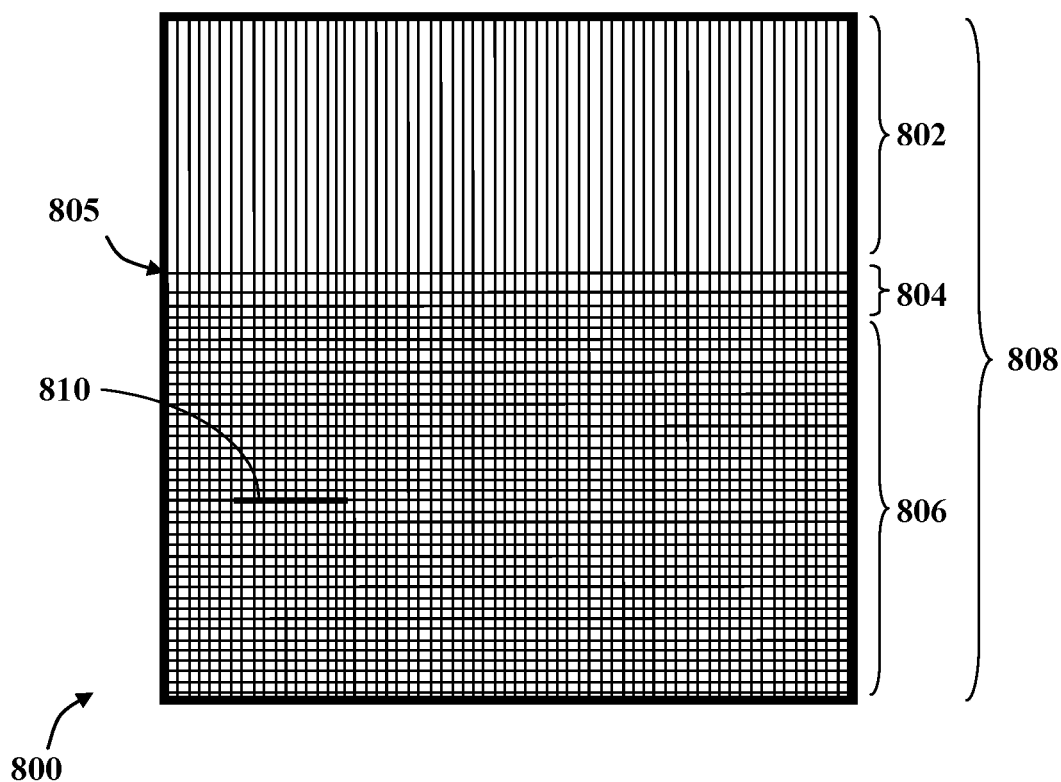
Fig. 8A
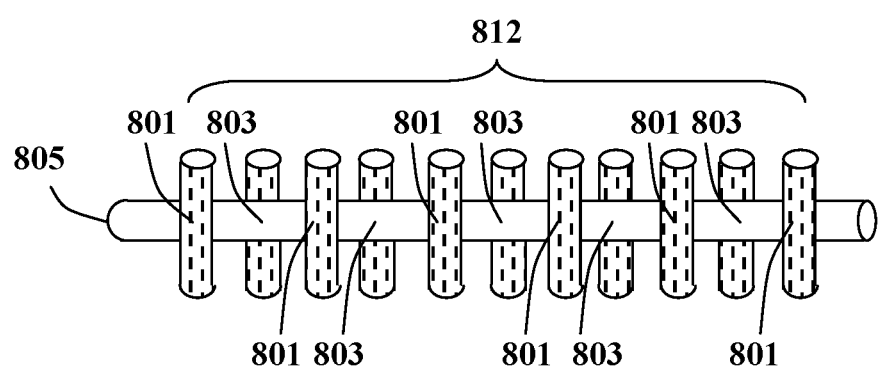
Fig. 8B
{1,0,1,0,1,0,1,0,1,0,1}
Fig. 8C

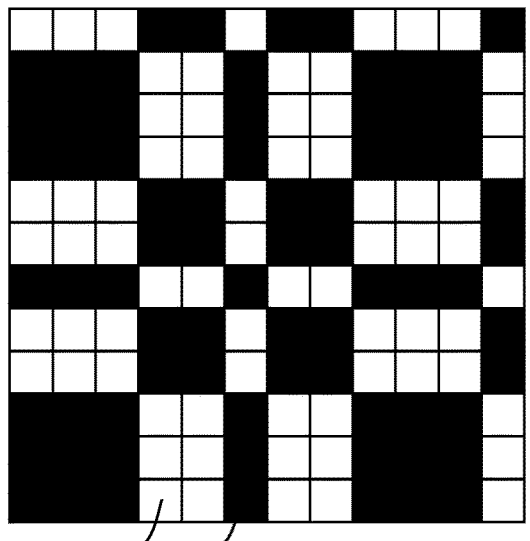
973 971
Fig. 9A
| | | | | | | | | | | | |
|---|---|---|---|---|---|---|---|---|---|---|---|
| 912 | 0 | 0 | 0 | 1 | 1 | 0 | 1 | 1 | 0 | 0 | 0 | 1 |
| 911 | 1 | 1 | 1 | 0 | 0 | 1 | 0 | 0 | 1 | 1 | 1 | 0 |
| 910 | 1 | 1 | 1 | 0 | 0 | 1 | 0 | 0 | 1 | 1 | 1 | 0 |
| 909 | 1 | 1 | 1 | 0 | 0 | 1 | 0 | 0 | 1 | 1 | 1 | 0 |
| 908 | 0 | 0 | 0 | 1 | 1 | 0 | 1 | 1 | 0 | 0 | 0 | 1 |
| 907 | 0 | 0 | 0 | 1 | 1 | 0 | 1 | 1 | 0 | 0 | 0 | 1 |
| 906 | 1 | 1 | 1 | 0 | 0 | 1 | 0 | 0 | 1 | 1 | 1 | 0 |
| 905 | 0 | 0 | 0 | 1 | 1 | 0 | 1 | 1 | 0 | 0 | 0 | 1 |
| 904 | 0 | 0 | 0 | 1 | 1 | 0 | 1 | 1 | 0 | 0 | 0 | 1 |
| 903 | 1 | 1 | 1 | 0 | 0 | 1 | 0 | 0 | 1 | 1 | 1 | 0 |
| 902 | 1 | 1 | 1 | 0 | 0 | 1 | 0 | 0 | 1 | 1 | 1 | 0 |
| 901 | 1 | 1 | 1 | 0 | 0 | 1 | 0 | 0 | 1 | 1 | 1 | 0 |
900
Fig. 9B
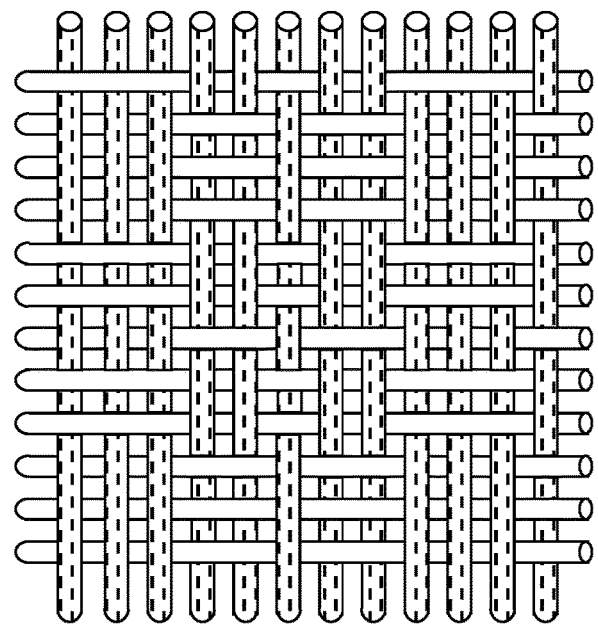
Fig. 9C

METHOD AND SYSTEM FOR LINE-BY-LINE ONE DIMENSIONAL FABRIC INSPECTION

CROSS-REFERENCE TO RELATED APPLICATIONS

This application is a U.S. National-Phase Application under 35 U.S.C. 371 of International Application No. PCT/IB2019/057031, which has an international filing date of Aug. 21, 2019, and which claims priority and benefit from U.S. Provisional Patent Application No. 62/723,802, filed Aug. 28, 2018, the contents and disclosure of which are incorporated herein by reference in their entirety.

TECHNICAL FIELD

The invention relates to systems and methods for on-loom fabric inspection. In particular, the invention relates to line-by-line pick inspection.

BACKGROUND ART

Weaving is the most popular way of fabric manufacturing. It is primarily done by interlacing two orthogonal sets (warp and weft) of yarns in a regular and recurring pattern. Weaving involves repeating in sequence the operations of shedding, picking, and battening. All these processes are typically carried out by a loom. Shedding is the process by which warp yarns are raised or lowered to produce a space, known as the shed, through which a filler yarn may be passed. Picking is the process of inserting a filler yarn through the shed, such that it intersects the warp threads. Battening is the process of pressing the filler yarn against a fell, where the newly woven fabric is formed.

A number of faults occur in fabric during weaving process. Woven fabric faults include cut yarn, double yarn, hole, float, stain, etc. The quality of woven fabric depends upon the number of defects left in the fabric after the manufacturing process. Defects developing during any of the above-mentioned processes determine the quality of the finished fabric. Typically, the finished fabric is inspected for faults and graded by a quality index according to industry standards. For example, in the standard four-point system of fabric inspection, penalty points being given for detected defects. The size of the penalty depends also upon the length of the defect with 1 penalty point being given to defects of 3 inches or less, 2 penalty points being given to defects of between 3 to 6 inches, 3 penalty points being given to defects of between 6 to 9 inches and 4 penalty points being given to defects of above 9 inches. The quality of the batch of cloth is described by the number of penalty points per 100 yards of inspected cloth, with up to 40 points being generally considered an acceptable defect rate. Apart from the four-point system described above, other standard indices, such as the more complicated ten-point system or the Dallas System for knitted fabric, may be used to measure the quality of cloth.

Conventionally, manual inspection is done for the finished fabric. Through manual inspection, generally, a sample size of at least ten percent of a roll of finished fabric is inspected. Faults in uninspected rolls are typically left undetected until the cloth is sold on. Furthermore, although such defect inspections are standardized as far as possible, it is noted that they depend upon the subjective assessment of the inspector. What one inspector may consider being a defect, another inspector may consider being acceptable. Accordingly, the same roll of cloth may be assessed very differently by different inspectors regardless of its actual quality.

The use of technology has improved the way of fault detection during various stages of a fabric manufacture. The highly efficient techniques of image capturing and image analysis enable the inspection of a woven fabric.

By way of example, International Patent Publication Number WO2006117673 to Gironi Pietro titled, "Apparatus and method for in-line reading and control of warp threads in a loom" describes an apparatus and method for reading and controlling warp threads, using a device to read images, and to compare between the acquired images and one or more predetermined samples in order to determine defects in the work cycle in order to instantly cut off the operation of the loom in response to the determined defect.

In another example, U.S. Pat. No. 9,909,238 to Wolf, Markus and Ackermann, Armin titled, "Monitoring device for a weaving machine, weaving machine, and method for monitoring" describes a monitoring device including a camera and a weft-thread beat-up device. The weft-thread beat-up device includes a reed or batten extending along the weft-thread beat-up device. The camera is fastened to the weft-thread beat-up device and includes adjacent sensor elements arranged in a row that extends parallel to the longitudinal direction of the weft-thread beat-up device.

In still another example, U.S. Pat. No. 5,165,454 to Kabushiki Kaisha Toyoda Jidoshokki Seisakusho and Kabushiki Kaisha Toyota Chuo Kenkyusho titled, "Detection of warp in reed dent before loom start up" describes a warp insertion monitoring method and apparatus for protecting woven cloth against defects due to warp insertion error or failure. A warp detector on a loom detects the presence or absence of the warp such that abnormalities in the positions at which warps are inserted through the reed are identified. Notably, in this system, timing for the warp detection is particularly selected to fall within a period during which the loom is stopped, so that the presence or absence of errors can be detected before the loom is restarted.

The need remains for an improved technology to detect faults through the on-loom fabric inspection system in fast and cost-effective manner. The systems and methods described herein come to address this need.

SUMMARY OF INVENTION

It is one aspect of the invention to introduce an on-loom inspection system comprising: at least one imaging device configured to collect images of at least one section of a weaving area of a loom; at least one image processor configured and operable to detect irregularities in image data; and at least one frame grabber configured and operable to receive images of at least a fell-pick from the imaging device and to send a compact image data package to the image processor; wherein the compact image data package comprises a characteristic sequence of warp-risers and warp-sinkers along the fell-pick. Optionally, the system may further comprise at least one image-capture trigger-mechanism operable to trigger the imaging device to capture an image at a required instant during the weaving cycle.

In another aspect of the invention, a method is taught for inspecting woven fabric. The method may include providing an on-loom fabric inspection system; obtaining a reference matrix representing a required weaving pattern, the reference matrix comprising a two dimensional array of values arranged as a sequence of rows, each row corresponding to a series of required warp-risers and required warp-sinkers along a single pick; capturing an image of a fell-pick along a fell line of the weaving area; identifying in the image a characteristic sequence of warp-risers and warp-sinkers along the fell-pick; generating a digital string corresponding to the characteristic sequence; and comparing the digital string with a corresponding row of the reference matrix.

Typically, the digital string comprises a sequence of binary or Boolean values. Additionally or alternatively, the digital string comprises a sequence of values further indicating color.

Where appropriate, the step of capturing the image of the pick further comprises: capturing an image of at least one section of a weaving area; transferring image data to at least one image processor; and identifying the pick within the image data. Optionally, the imaged section of weaving area comprises all of a shed region, a woven fabric region and a fell region.

Additionally or alternatively, the method further comprises: providing at least one imaging device configured to collect images of at least one section of a weaving area of a loom; providing at least one image-capture trigger-mechanism; selecting a required instant during the weaving cycle; and the at least one image-capture trigger-mechanism triggering the imaging device at the required instant during the weaving cycle. Accordingly, the required instant may be selected to coincide with the moment that the shed is open.

Optionally, the method further comprises generating an accuracy metric based upon deviations of the digital string with the corresponding row of the reference matrix. Optionally, the accuracy metric indicates the presence of a weaving defect. Alternatively, or additionally, the method may include generating a standard quality index for the woven fabric.

Where required the method may further initiate an automatic correction process when the accuracy metric lies beyond a threshold value. For example, the automatic correction process may be selected from at least one of a group consisting of: stopping the loom, unweaving the cloth, adjusting battening force, producing an alert and the like as well as combinations thereof.

Variously, the step of obtaining a reference matrix comprises accessing a reference pattern stored in a memory component. Additionally or alternatively, the step of obtaining a reference matrix comprises: monitoring an ongoing weaving process; identifying a repeated cycle in the weaving process; generating the reference matrix according to the repeated cycle; and storing the reference matrix in a memory component.

It is a particular aspect of the disclosure to teach a method further comprising: providing at least one imaging device configured to collect images of at least one section of a weaving area of a loom; providing a frame grabber configured and operable to receive images from the imaging device; providing an image processor; and sending a compact image data package to the image processor.

Typically, the compact image data package comprises a sequence of Boolean values representing the characteristic sequence of warp-risers and warp-sinkers along the fell-pick. Additionally or alternatively, the compact image data package comprises a sequence of values representing a section of a captured image including only a reduced section of the shed region, the fell-pick and a section of the fell region.

BRIEF DESCRIPTION OF DRAWINGS

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the several selected embodiments may be put into practice.

In the accompanying drawings:

FIG. 1 illustrates a schematic side view of an exemplary configuration of an on-loom fabric inspection system integrated onto a loom;

FIG. 2 illustrates the schematic side view of the fabric inspection system of FIG. 1 with an image capturing device focused to take images of a fell region and a newly woven fabric;

FIG. 3 illustrates the schematic side view of the fabric inspection system of FIG. 1 with an image capturing device focused to take images of warp yarns in a shed;

FIG. 4 is a block diagram representing the main components of a first embodiment of an on-loom fabric inspection system;

FIG. 5 illustrates a schematic side view of an exemplary configuration of an on-loom fabric inspection system of the invention;

FIG. 6 illustrates the schematic side view of the fabric inspection system of FIG. 5 with an image capturing device focused to take images of a weaving area;

FIG. 7 is a flowchart representing a method for detecting defects in woven fabric using the on-loom fabric inspection system;

FIG. 8A is a representation of one frame imaged by the image capturing device of the on-loom fabric inspection system;

FIG. 8B represents a section of the fell-pick yarn interwoven between a set of warp threads;

FIG. 8C shows a one dimensional array of Boolean values representing the characteristic sequence of warp-risers and warp-sinkers;

FIG. 9A represents a weaving pattern;

Figure 10A:
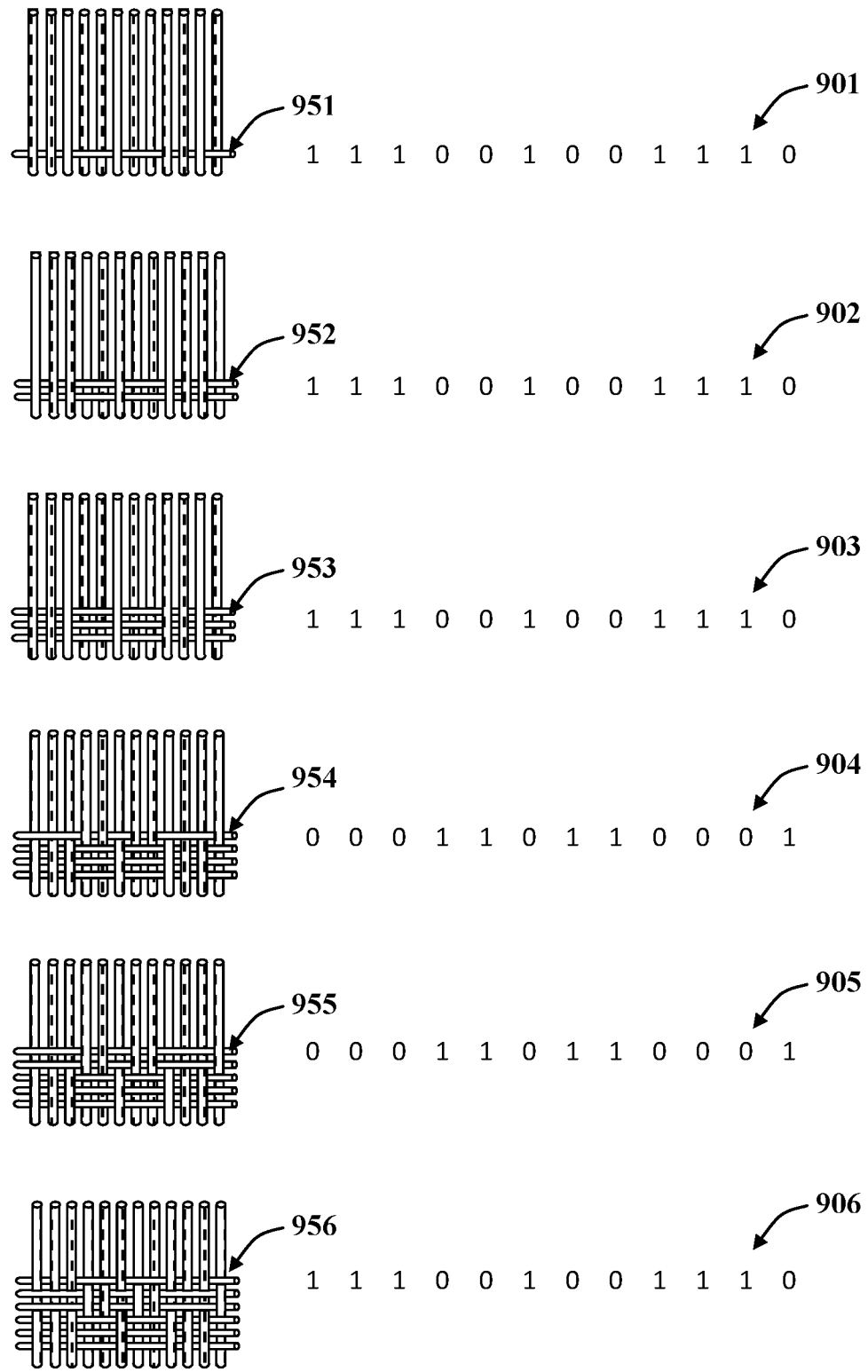
Figure 10B:
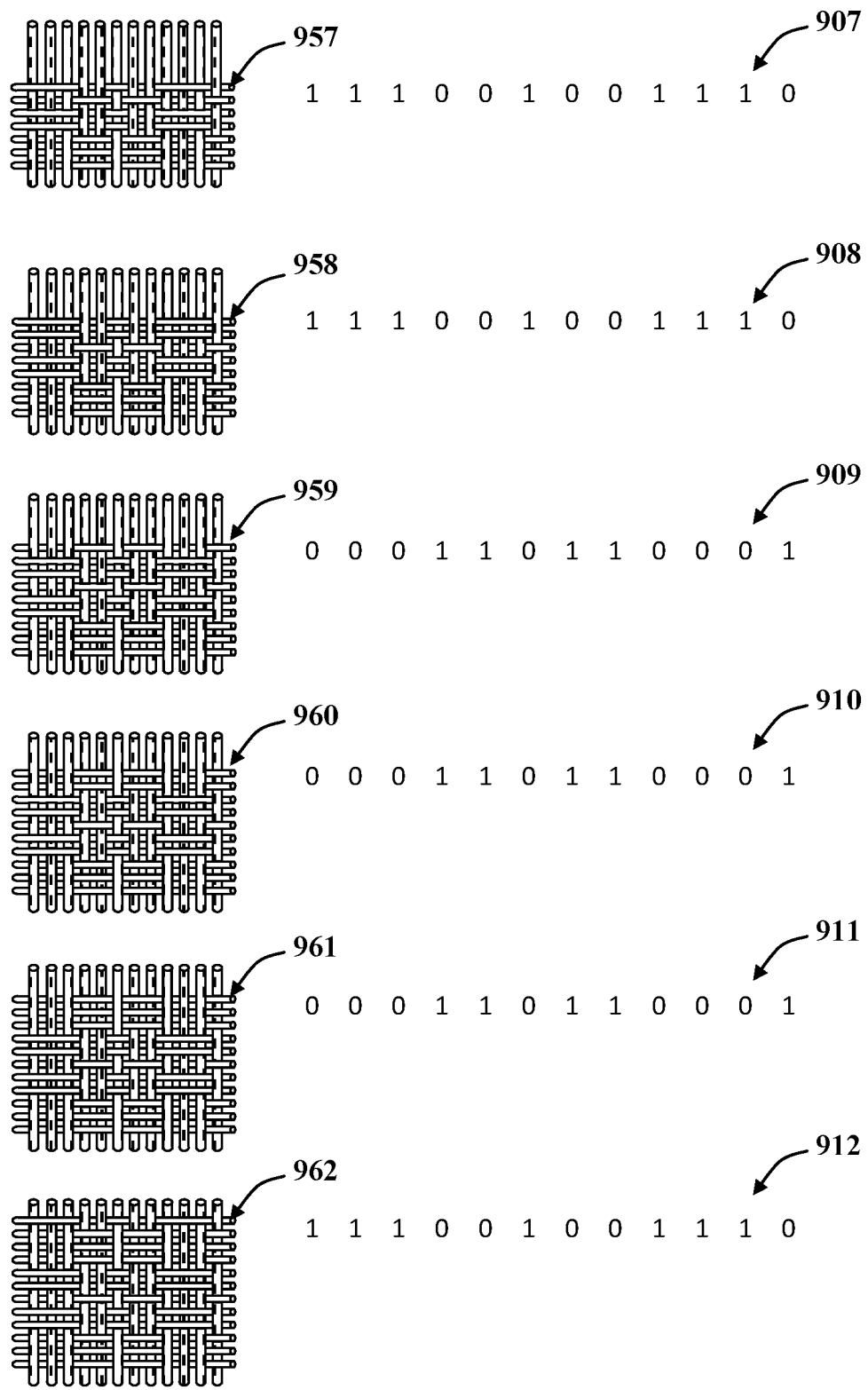
Figure 11:
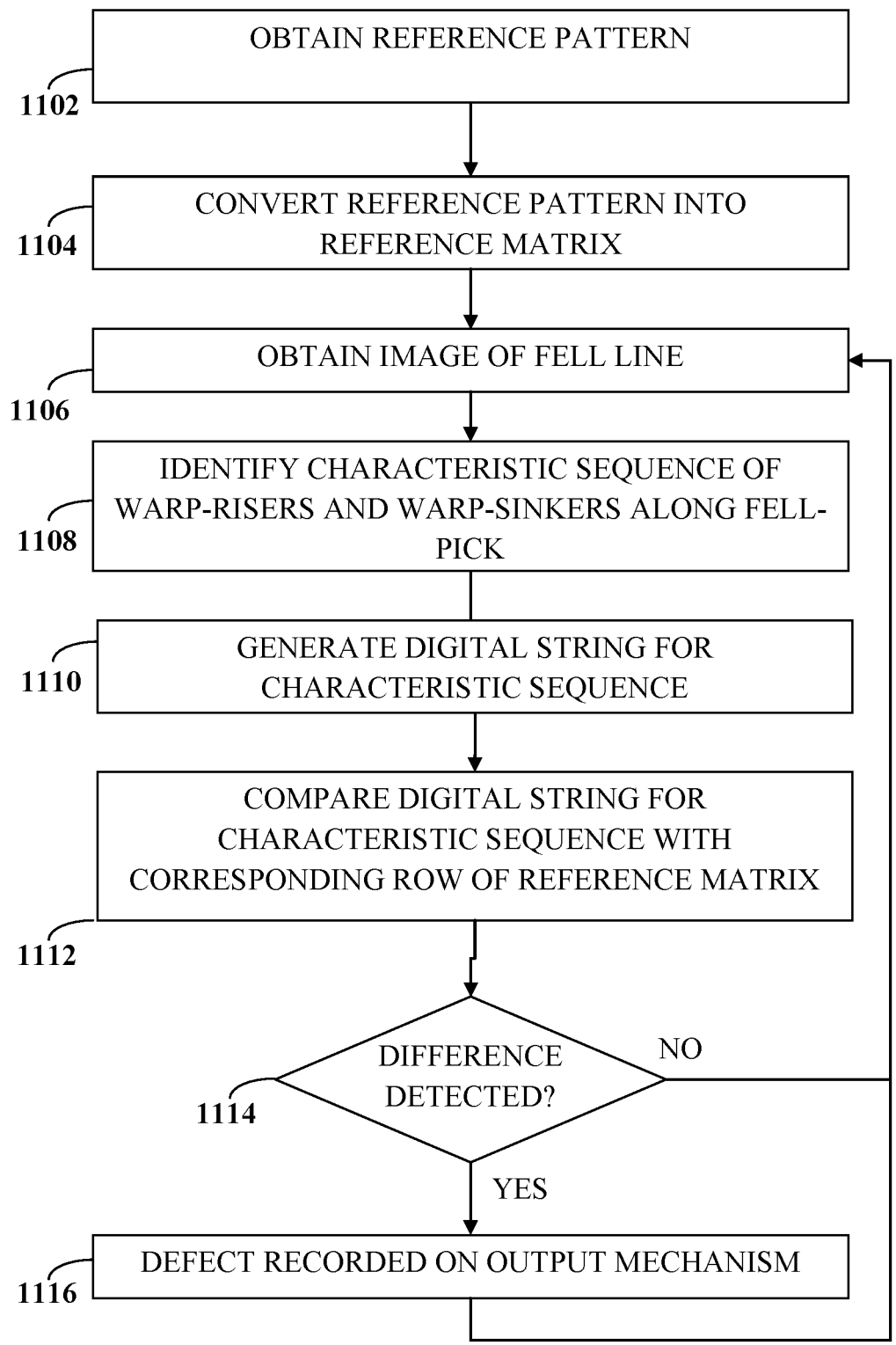

FIG. 9B represents a reference matrix corresponding to the weaving pattern of FIG. 9A;

FIG. 9C represents a woven fabric following the weaving pattern of FIG. 9A;

FIGS. 10A and 10B show a sequence of added picks alongside their corresponding rows from the reference matrix: and FIG. 11 is a flowchart illustrating a method for detecting anomalies during weaving.

DESCRIPTION OF EMBODIMENTS

Aspects of the present disclosure relate to systems and methods for on-loom fabric inspection.

As required, detailed embodiments of the present invention are disclosed herein; however, it is to be understood that the disclosed embodiments are merely examples of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

As appropriate, in various embodiments of the disclosure, one or more tasks as described herein may be performed by a data processor, such as a computing platform or distributed computing system for executing a plurality of instructions. Optionally, the data processor includes or accesses a volatile memory for storing instructions, data or the like. Additionally or alternatively, the data processor may access a non-volatile storage, for example, a magnetic hard disk, flash-drive, removable media or the like, for storing instructions and/or data.

It is particularly noted that the systems and methods of the disclosure herein may not be limited in its application to the details of construction and the arrangement of the components or methods set forth in the description or illustrated in the drawings and examples. The systems and methods of the disclosure may be capable of other embodiments, or of being practiced and carried out in various ways and technologies.

Alternative methods and materials similar or equivalent to those described herein may be used in the practice or testing of embodiments of the disclosure. Nevertheless, particular methods and materials are described herein for illustrative purposes only. The materials, methods, and examples are not intended to be necessarily limiting. Accordingly, various embodiments may omit, substitute, or add various procedures or components as appropriate. For instance, the method steps may be performed in an order different from described, and various steps may be added, omitted or combined. In addition, aspects and components described with respect to certain embodiments may be combined in various other embodiments.

Figure 1:
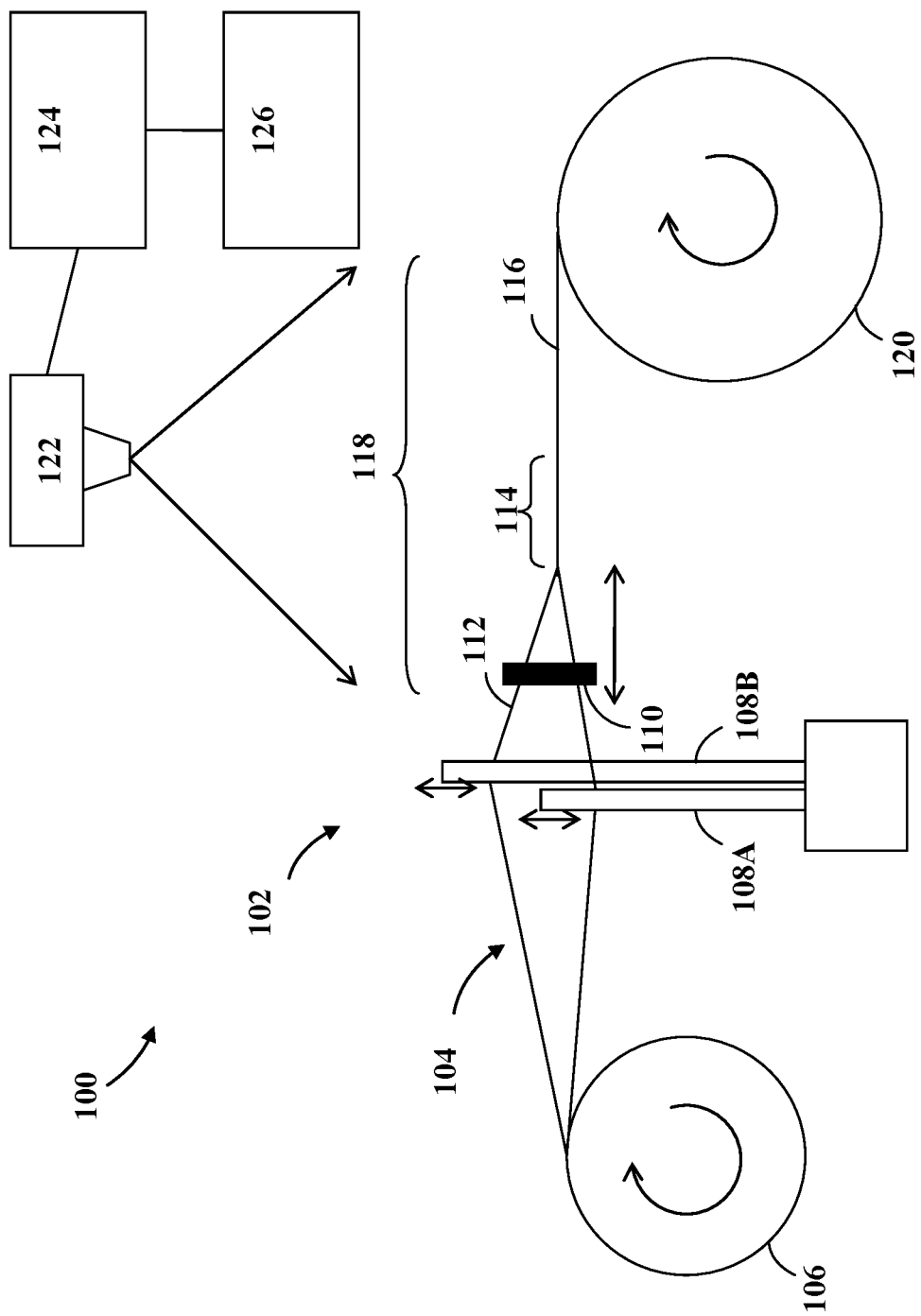

FIG. 1 represents an exemplary configuration of an on-loom fabric inspection system 100. A loom 102 includes a yarn roll 106, a take-up roll 120, a pair of heald frames 108A and 108B and a reed 110. An array of warp yarns 104 are threaded through the heald frames 108A and 108B and the reed 110. The heald frames 108A and 108B are made of wood or metal such as aluminium. They carry a number of heald wires (not shown) through which the ends of the warp yarns pass. The heald frames 108A and 108B are configured to raise and lower the warp yarns, thereby producing a shed 112 through which a filler yarn (not shown) may be inserted using some filling insertion mechanism (not shown) such as a shuttle, rapier, jet or the like. The reed 110 is a metallic comb used to batten the filler yarn against newly woven fabric 116. It also helps to maintain the position of the warp yarns 104. The woven fabric 116 is collected by the take-up roll 120 as it is produced.

The on-loom fabric inspection system 100 is configured to monitor a weaving area 118 including the newly woven fabric 116, the shed 112 and a fell region 114. The fell region 114 is a section of the weaving area 118 where the reed 110 strikes a weft yarn along a fell line during the operation of the loom 102. The fell line is the boundary beyond which the fabric 116 has been woven. The fabric inspection system 100 includes one or more image capturing devices 122 in communication with an image processor 124. Exemplary image capturing device 122 includes an analog or digital still image camera, a video camera, an optical camera, a laser camera, a laser or 3D image scanner, or any other device capable of capturing high resolution images of the weaving area 118. The image capturing device 122 can also be a high definition inbuilt camera of a communication device such as a computer, a laptop or a mobile phone. In an exemplary embodiment, to capture the images of high speed working loom, the camera required needs to be of very high speed, for example capturing more than 1000 frames/second. The image processor 124 is operable to receive and process data collected by the image capturing devices 122. The image processor 124 can be a server computer, a client user computer, a personal computer (PC), a tablet PC, a laptop computer, a desktop computer, a mobile phone, a control system and a network router, switch or bridge. Alternatively, the image processor 124 can be software application running on a virtual cloud environment. An output mechanism 126 such as a visual display unit associated with the image processor 124 may provide information to a user regarding the functioning of the loom 102 and upon detection of any fault. The information may be provided in form of images, graphical representations, numbers or text, and can relate to measurement data, statistical data, etc. The output mechanism 126 may also display an alert or a flag in case any deviation from the normal operation of the loom 102 is detected. It is noted that such a configuration of the on-loom fabric inspection system 100 may be operable to monitor the weaving area 118 during operation of the loom 102. Accordingly, a computer may be connected to the loom 102 and operable to stop the loom 102 or otherwise adjust the loom 102 settings in response to data gathered from the monitored weaving area 118.

Figure 2:
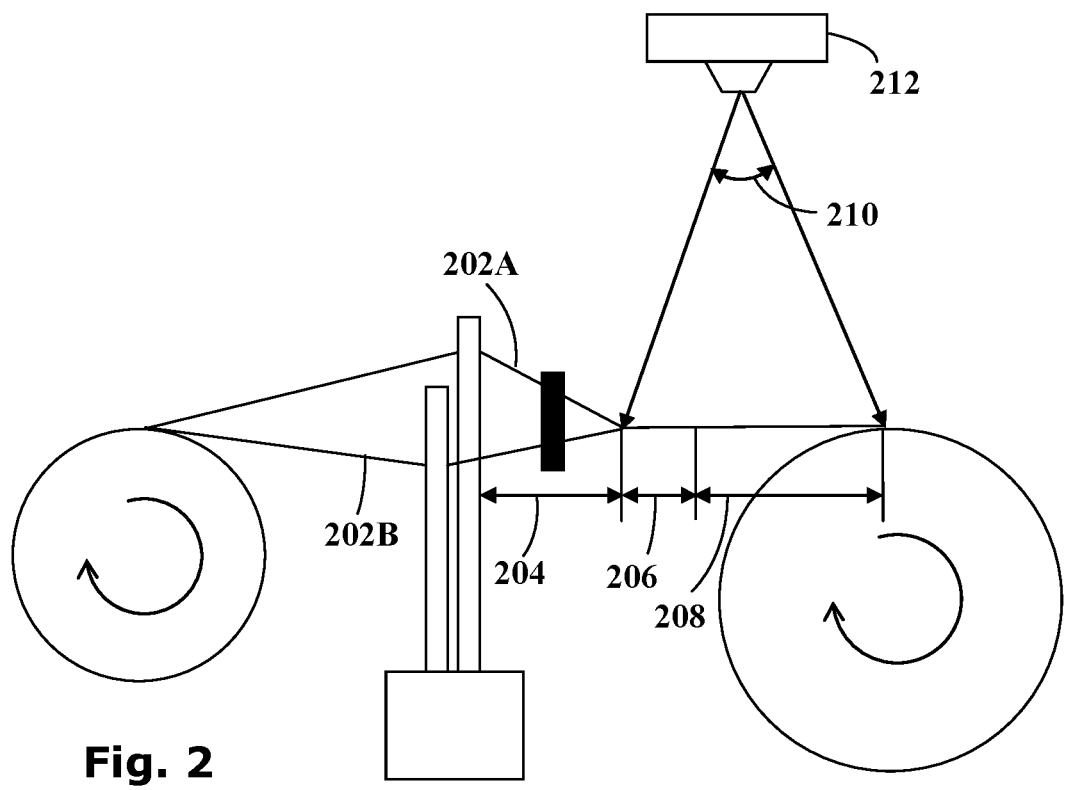
Figure 3:
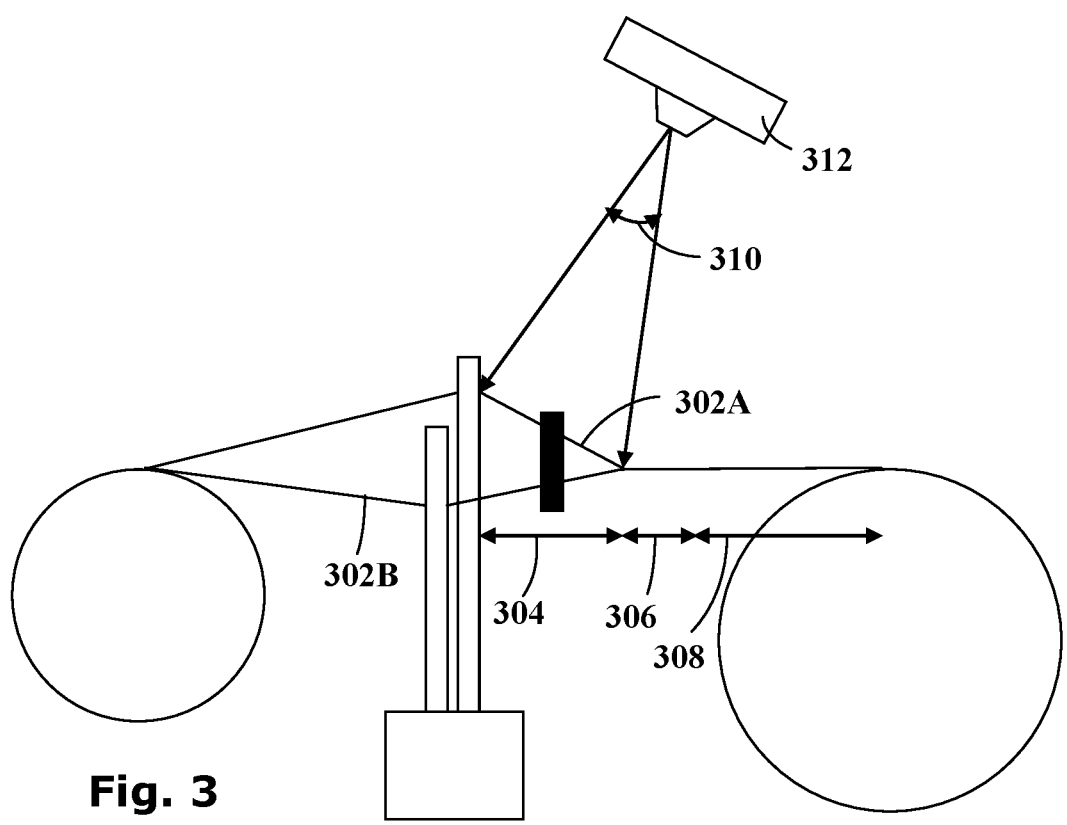

Conventionally, the on-loom fabric inspection system 100 captures the images of the weaving area 118 when the heald frames 108A and 108B are separate. In such a state, since the warp yarns 112 and the fell region 114 are not coplanar with each other, it is not possible to focus on both the warp yarns 112 in the shed and the fell region 114. Therefore, the object distance of image capturing device 122 needs to be adjusted to capture images of either warp yarns 112 or the fell region 114. FIG. 2 illustrates an exemplary embodiment where the image capturing device 212 is focused to take images of the fell region 206 and the region 208 of the newly woven fabric. In this case the image capturing device 212 cannot capture the images of the warp yarns 202A, 202B in the shed region 204. FIG. 3 illustrates another exemplary embodiment where the image capturing device 312 is focused to take images of the warp yarns 302A, 302B in the shed region 304. In this case the image capturing device 312 cannot capture the images of the fell region 306 and the region 308 of the newly woven fabric.

As a remedial measure, multiple image capturing devices focused on different regions 204, 206, 208 (or 304, 306, 308) may be used. However, this increases the cost and time for separate analysis of the images.

Figure 4:
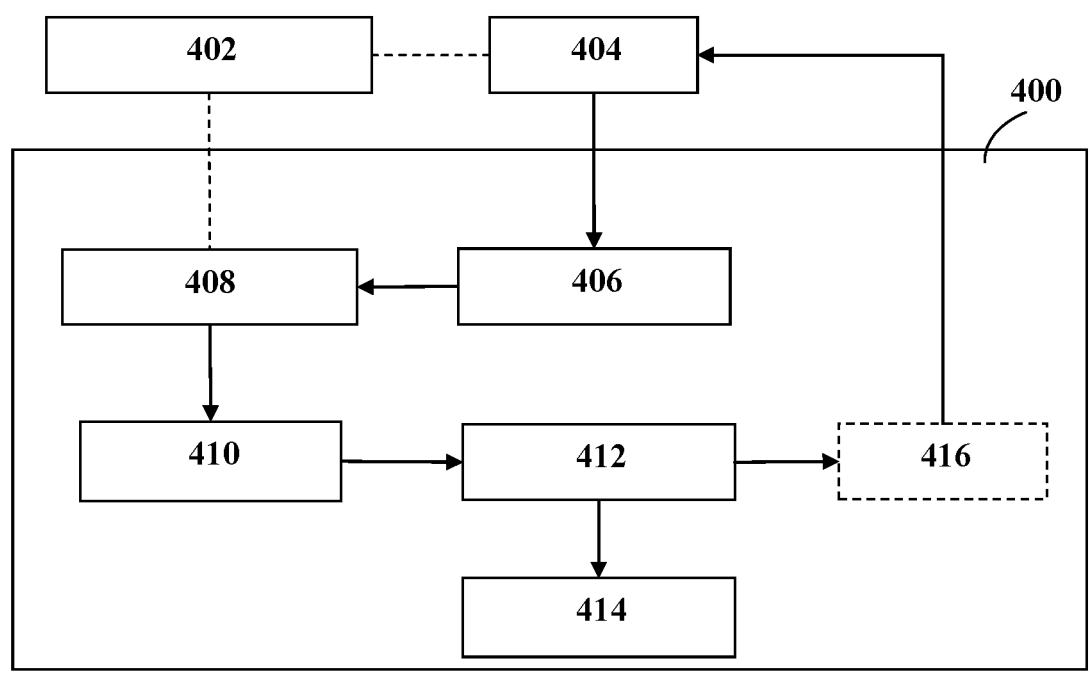

Reference is now made to the block diagram of FIG. 4, which represents the main components of an on-loom fabric inspection system 400 according to the invention. The system 400 may identify faults during the process of fabric manufacture, thereby enabling early detection or prevention of fabric defects. On-loom systems 400 such as described herein may serve as a cost-effective tool for providing continuous monitoring of woven textiles during production and may provide an industry standard for quality control of such fabrics.

The on-loom fabric inspection system 400 includes an image-capture trigger-mechanism 406, an image capturing device 408, an image processor 410, a controller 412 and an output mechanism 414. The image-capture trigger-mechanism 406 is configured to trigger the image capturing device 408 based on a required condition. The image capturing device 408 is configured to collect image data from a weaving area 402 of a loom 404 and to transfer this data to the image processor 410.

Various types of image capturing device 408 may be used which suits the requirement. Exemplary image capturing device 408 includes an analog or digital still image camera, a video camera, an optical camera, a laser camera, a laser or 3D image scanner, or any other device capable of capturing high resolution images of the weaving area 402. The image capturing device 408 can also be a high definition inbuilt camera of a communication device such as a computer, a laptop or a mobile phone. In an exemplary embodiment, to capture the images of a high speed working loom, the camera required needs to be of very high speed, like capturing more than 1000 frames/second. Further, an array camera or the like may be used having a resolution suitable to detect individual yarns within woven fabric. Resolution of the image capturing device 408 may be selected according to the cost and nature of the inspected fabric. The resolution may be less than 1 millimeter, e.g., around 0.1 millimeter as required.

The image-capture trigger-mechanism 406 may include a detector or sensor connected to the loom 404 and configured to detect the movement of heald frames 508A and 508B (shown in FIG. 5) of the loom 404. Accordingly, the image capturing device 408 may be triggered by the detector when the required condition is met for the heald frames. An exemplary detector may include a mechanical sensor, an electrical sensor, or an optical sensor. It should be noted that the scope of the invention should not be limited with the exemplary detectors described above and any other detector which can detect the motion of the heald frames can be used for the purpose.

In another embodiment, the image-capture trigger-mechanism 406 may additionally or alternatively include a timer such as a stroboscopic light or lamp which can be timed to produce a flash of light when the required condition is met for the heald frames.

In still other embodiments, the image-capture trigger-mechanism 406 may additionally or alternatively include a receiver in communication with the loom 404 and configured to receive output signals from an encoder of the loom engine. For example, a communication cable may be connected between an output terminal of the loom 404 and an input terminal of the image-capture trigger-mechanism 406. Accordingly trigger signals may be sent when the required condition is met, for example the image-capture trigger-mechanism 406 may receive a pick signal indicating that the picking process has been initiated and the picking signal may serve as a trigger signal for the image capturing device 408.

The image data collected by the image capturing device 408 is sent to the image processor 410 which may analyze the received image data and identify irregularities indicative of weaving faults. Various image processors 410 may be used with the system 400. A processor, such as a computer, a field programmable gate array (FPGA), an application specific integrated circuit and a microprocessor may be selected to provide image processing at sufficiently fast rate. The processing rate may be fast enough to allow each frame imaged by the image capturing device 408 to be analyzed in real time. Optionally, the image processor 410 may be operable to segment each frame and to analyze each frame segment separately and possibly with individual sampling rates. Exemplary image processor 410 includes a server computer, a client user computer, a personal computer (PC), a tablet PC, a laptop computer, a desktop computer, a mobile phone, a control system and a network router, switch or bridge. Alternatively, the image processor 410 can be a software application running on a virtual cloud environment.

The controller 412 is provided to respond to the detection of weaving faults. The controller 412 may respond, for example, by outputting data to the output mechanism 414. The output mechanism 414 such as a visual display unit associated with the image processor 124 may provide information to a user regarding the functioning of the loom 102 and upon detection of any fault. The information may be provided in form of images, graphical representations, numbers or text, and can relate to measurement data, statistical data, etc. The output mechanism 414 may also display an alert or a flag in case any deviation from the normal operation of the loom 404 is detected. The output mechanism 414 may also comprise a database to store the processed data of images. Where required, the controller 412 may be further operable to activate an override switch 416 to stop or otherwise adjust the loom 404 in response to the detection of defects. The override switch 416 may be an actuator or any other system which suits the requirement.

In one of the embodiments of the present invention, the image-capture trigger-mechanism 406 is conditioned to trigger the image capturing device 408 when the heald frames 508A and 508B (shown in FIG. 5) are aligned with each other and trigger the image capturing device 408 at that instance to capture images of the weaving area 402. In such a situation, the warp yarns in the shed are coplanar with the fell region and the newly woven fabric.

Figure 5:
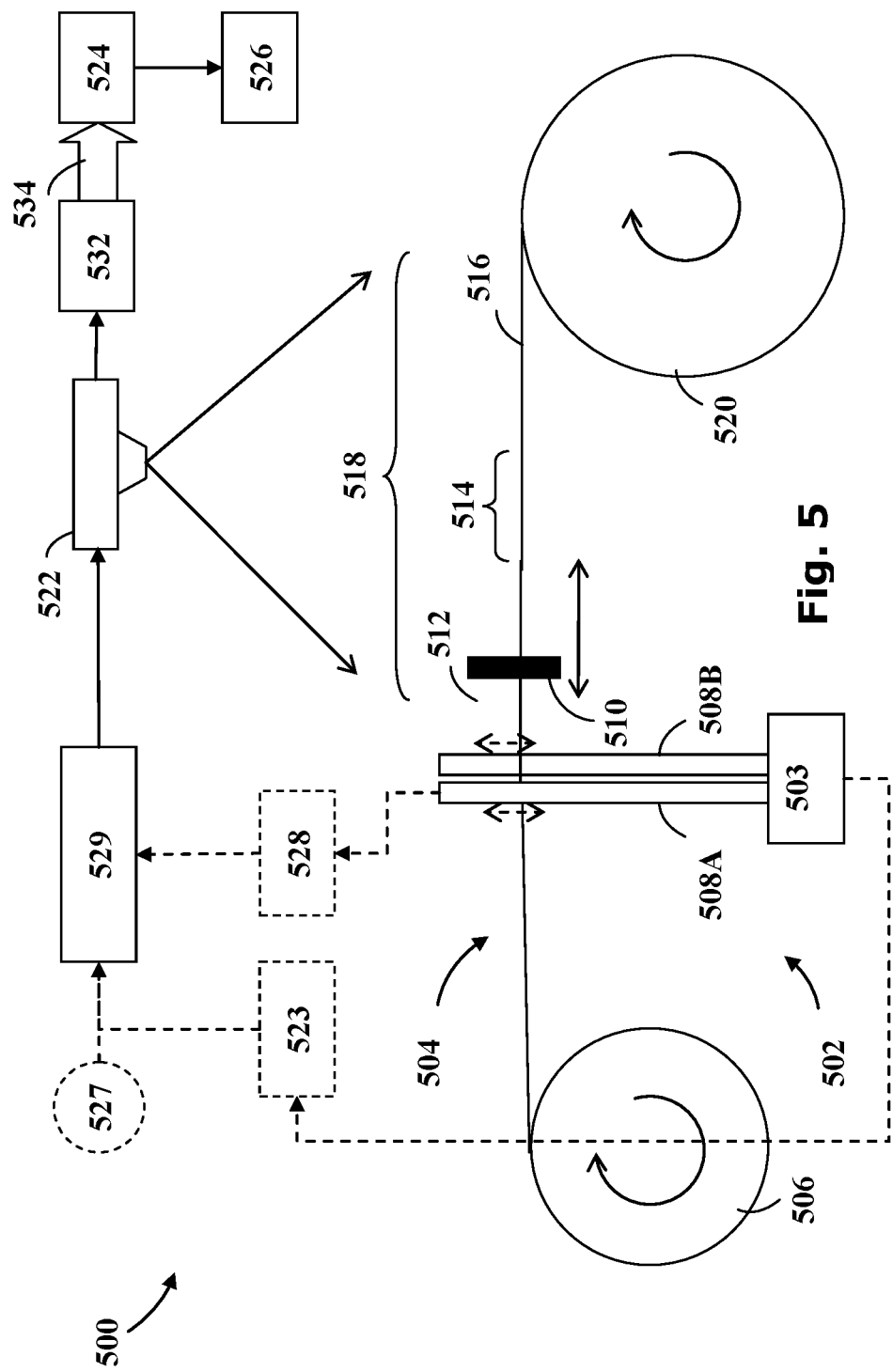

Reference is now made to FIG. 5 which shows a schematic side view of an exemplary configuration of a fabric inspection system 500 according to the invention, integrated onto a loom 502.

The configuration of the loom 502 of FIG. 5 is similar to FIG. 1 with the exception that the heald frames 508A and 508B are depicted at the same level and aligned with each other. Upper and lower warp yarns in a shed 512 are in the same plane as a fell region 514 of a cloth and a newly woven fabric 516. The capturing of images of weaving area 518 enables a single object distance of image capturing device 522 to be used to image both regions, the shed region 512 and the fell region 514, allowing irregularities to be detected in both. A detector 528 is included in the system 500 for the purpose. Preferably, in each movement cycle (up and down) of the heald frames 508A and 508B, the images of weaving area 518 are captured twice in order to capture both sets of warp yarns. The detector 528 may variously comprise a sensor such as a mechanical sensor, an electrical sensor, an optical sensor and the like, as well as combinations thereof.

Figure 6A:
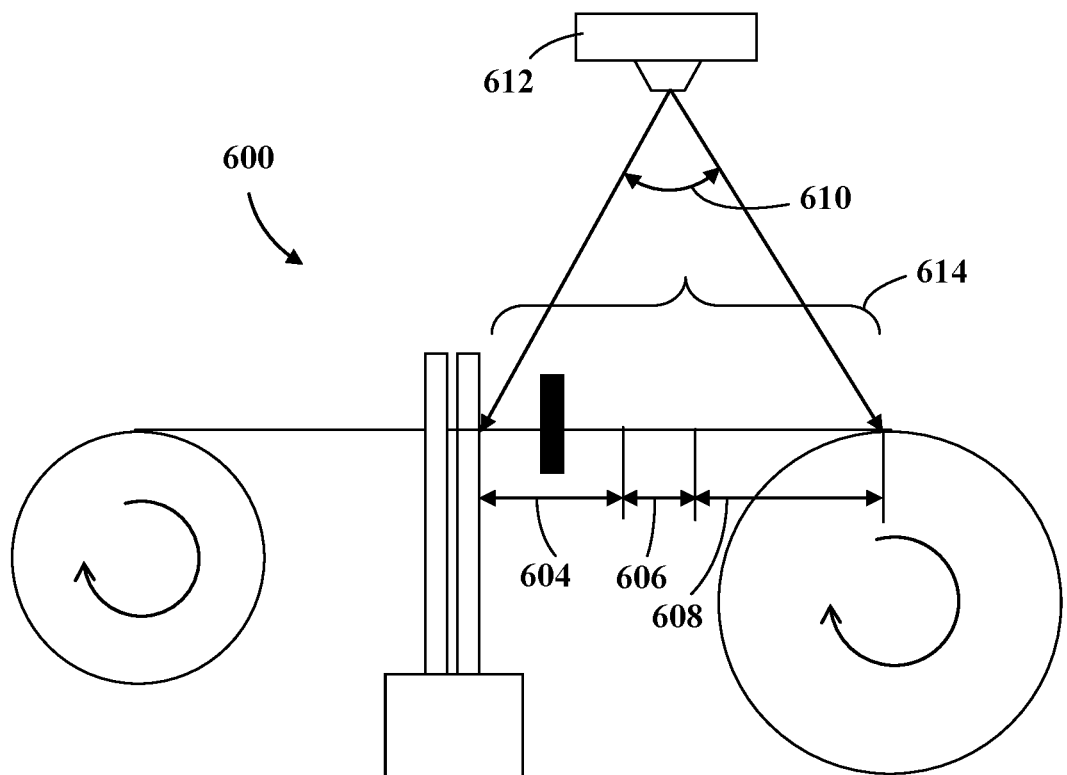

FIG. 6A illustrates the schematic side view of a fabric inspection system 600 with an image capturing device 612 focused to take images of a weaving area 614. Since upper and lower warp yarns in shed 604 are in same plane as fell region 606 and newly woven fabric 608, the image capturing device 612 can use a single depth of focus over a wide angle 610 to capture the image of the complete weaving area 614.

Figure 6B:
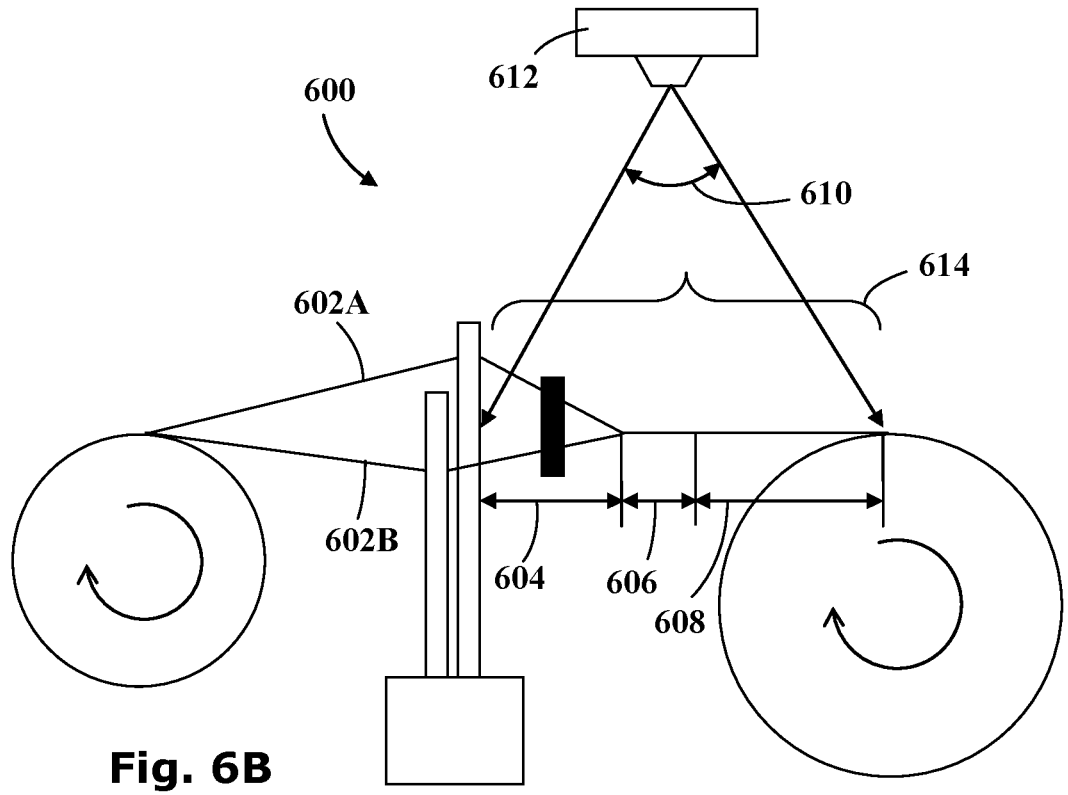

FIG. 6B illustrates another configuration of the fabric inspection system 600 in which the heald frames are separated so as to raise the upper warp yarns 602A and lower the lower warp yarns 604B, thereby creating the shed. It is particularly noted that where appropriate, images may be additionally or alternatively captured in this configuration. Accordingly, the image capturing device 612 may image only the upper warp yarns 602A, thereby enabling the image processor 410 (shown in FIG. 4) to distinguish more readily between warp-risers and warp-sinkers along the fell-pick yarn.

Referring back to FIG. 5, in still another alternative embodiment, an image-capture trigger-mechanism 529 may optionally trigger the image capturing device 522 in other ways. For example, an image-capture trigger-mechanism 529 may include a timer 527 such that the shutter of the image capturing device 522 can be set for a fixed time to capture images of the weaving area 518. The shutter timing can be set to the instance when the heald frames 508A and 508B are aligned with each other. The images of the weaving area 518 are captured at that instance without the need for being triggered by the detector 528.

Additionally or alternatively, the image-capture trigger-mechanism 529 may further include a receiver 523 in communication with the loom 502 and configured to receive output signals from an encoder of the loom engine 503.

Figure 7:
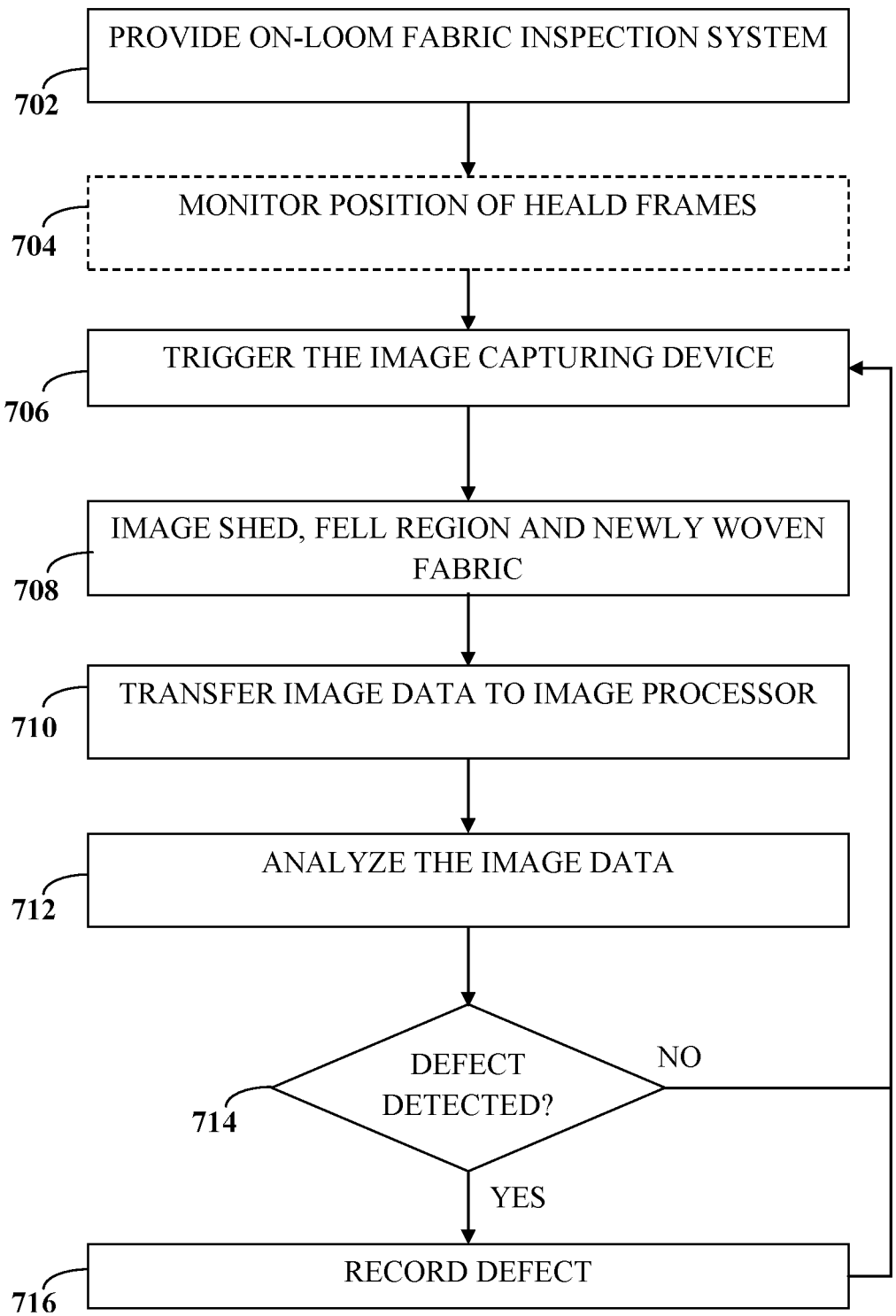

Reference is now made to the flowchart of FIG. 7 which illustrates exemplary method steps of the present invention for detecting defects in a woven fabric using the on-loom fabric inspection system 500.

The on-loom fabric inspection system 500 is provided at step 702. During the operation of the loom 502, optionally, at step 704, an image-capture trigger-mechanism 529, which may include a detector 528, may monitor the position of the heald frames 508A and 508B. The image capturing device 522 is triggered at a required point in the cycle, for example when the heald frames 508A and 508B are aligned with each other, at step 706. The image capturing device 522 then collects images of the weaving area 518, including the shed 512, the fell region 514 and the newly woven fabric 516, at step 708.

Image data is transferred to the image processor 524 at step 710. The image processor 524 analyzes the received image data for irregularities and faults at step 712. If an irregularity detected in the image data indicates at step 714 that a weaving fault has occurred, then this fault is recorded on the output mechanism 526 at step 716. The process may continue by another image being collected and analyzed, such that the process may be repeated.

Optionally the on-loom fabric inspection system 500 may further include a frame grabber 532 configured and operable to receive images from the imaging device 522 and to send a compact image data package 534 to the image processor 524.

It is noted that the recordation of the weaving fault may involve a simple fault count such as using a penalty point system such as the four-point for example. Alternatively more precise data relating to the types of faults detected and their statistical distribution for example may be recorded.

Referring to FIG. 8A, which shows the representation of one frame 800 of a weaving area 808 imaged by the image capturing device 522 of the on-loom fabric inspection system 500. The frame 800 shows the shed 802, the fell region 804 and the newly woven fabric 806. An oil spot, caused by a soiled section 810 propagating along the newly woven fabric 806 is also shown. The image frame 800 is processed by the image processor 524 to detect the soiled section 810 and appropriate measure can be taken by a loom operator to resolve the issue.

Weaving faults may occur in any of these areas of the frame 800 and may be detected using the on-loom fabric inspection system 500. For example, slubs, missing yarns, end outs and the like may be detected in the shed 802 and fell region 804 whereas oil spots, loom stop marks, start marks and the like may be detected in the newly woven fabric 806.

Various faults occurring in the weaving area 808 during manufacture may cause defects in the finished fabric. These include slubs, holes, missing yarns, yarn variation, end out, soiled yarns, wrong yarn faults, oil spots, loom-stop marks, start marks, thin place, smash marks, open reed, mixed filling, kinky filling, mixed end, knots, jerk-in, dropped picks, broken picks, double picks, double ends, drawbacks, burl marks and the like. It should be noted that the listed faults are exemplary in nature and should not limit the scope of the invention.

In other embodiments of the fabric inspection, a novel, line by line method for identifying faults may be used. According to this method, a reference pattern representing the desired pattern of the fabric may be obtained. Such a reference pattern may be converted, for example, into a two dimensional matrix including an array of values arranged in rows and columns.

By way of illustration, in a reference pattern for weaving, each column of the array may correspond to a warp end and each row may correspond to a pick or an individual filling yarn to be inserted through the shed during picking so as to intersect with the warp threads.

Although, in the interest of brevity, only a weaving pattern is described herein, it is further noted that such an inspection system may be adapted for use with other fabric types such as tufted fabrics and the like.

It is particularly noted that where required the reference matrix may consist of Boolean values. Thus, for example, in a weaving pattern, a ZERO value may be used to indicate a warp-riser where the warp thread overlies the weft, and a ONE value may be used to indicate a warp-sinker, where the warp thread under lies the weft. Alternatively the ZERO value may be used to indicate a warp-sinker and the ONE value may be used to indicate a warp-riser.

Referring again to FIG. 8A, using a fabric inspection system such as described herein, images are collected of the shed 802, fell region 804 and newly woven fabric 806. Accordingly, during each cycle of a loom, the fell-pick 805 may be identified either before or after battening. As used herein the term fell-pick refers to the last pick yarn to be inserted into the shed and is therefore the furthest pick from the woven fabric.

With reference to FIG. 8B which schematically represents a section of the fell-pick yarn 805 interwoven between a set of warp threads 812, it is a particular feature of the current method that the image of the fell-pick yarn 805 may be analyzed so as to identify its characteristic sequence of warp-risers 801 and warp-sinkers 803. As shown in FIG. 8C this characteristic sequence of warp-risers 801 and warp-sinkers 803 may be represented by a one dimensional array or digital string 820 of Boolean values.

It is noted that when the shed is in the open configuration, the contrast between the warp-risers and the warp-sinkers may be enhanced; accordingly, the image collection may be usefully timed to coincide with the point in the weaving cycle when the shed is open. It is also noted that the contrast between the warp thread and the weft thread may be further enhanced by adjusting illumination between over-shed illumination and under-shed illumination as required.

Alternatively or additionally, it may be desirable to capture the image of the fell-pick at the point in the cycle when the warp yarns in the shed are coplanar with the fell region and the newly woven fabric such as described herein.

The characteristic sequence of the imaged fell-pick may be compared with the corresponding row of the reference matrix to generate an accuracy metric The accuracy metric may be used to indicate the presence of a weaving defect and may be used in a defect calculation function to generate a standard quality index for the woven fabric.

Where the accuracy metric lies beyond a threshold value, automatic processes may be initiated such as, in a nonlimiting manner, stopping the loom, unweaving the cloth, adapting the force of the next battening cycle, producing an alert or the like.

By way of example, an accuracy metric may be determined by counting the number of errors occurring when either warp-risers or warp-sinkers do not match the corresponding values in the reference matrix. The Error Density may be determined, for example by counting the number of errors in a given length of fabric or within a given number of wefts. Thus fabric may be graded according to the Error Density, with fabric with fewer than one error in, say 100,000 wefts being a higher quality than fabric with fewer than one error in 50,000 wefts.

Additionally, or alternatively, an accuracy metric may be a weighted score, possibly assigning greater value to errors proximate to each other than errors more spaced apart. For example, the accuracy metric may be calculated by the calculation:

$$AM = \sum W_j E_j$$

where AM represents accuracy metric, $E_j$ represents a weighted error when a warp-riser or warp-sinker does not match the corresponding value in the reference matrix, $W_j$ represents the weighting coefficient of $E_j$, which may vary according to the proximity of the detected errors.

The value of the accuracy metric itself may serve as an input parameter of a defect calculation function which may be combined with other quality indications, such as the weft spacing function, dropped pick count, missing yarn count, slub count, oil spot count, loom stop count such as described in U.S. Pat. No. 9,499,926, which is incorporated herein by reference in its entirety, or other faults which will occur to those skilled in the art.

For example, a quality index may be determined by summing terms representing accuracy of weaving pattern, fault detection and weft spacing using a quality function such as:

$$Q = K_E \sum W_j E_j + K_f \frac{\sum W_i F_i}{N_f} + K_S \sum W_k S_k$$

where Q represents the calculated quality index value, $K_E$ represents a weighting factor for the accuracy metric, $F_i$ represents a count of a particular fault, $W_i$ represents the weighting coefficient of the particular fault type $F_i$, $N_f$ represents the number of fault counts being recorded, $K_f$ represents a weighting factor for the contribution of fault counts to the quality index, $S_k$ represents the value of a weft-spacing value, $W_k$ represents the weighting coefficient of each weft-spacing value $S_k$ and $K_f$ represents a weighting factor for the contribution of weft spacing deviation to the quality index.

It is noted that the above examples of quality function and accuracy matrix calculations are provided for illustrative purposes only and that other quality functions may be additionally or alternatively used as occur to those skilled in the art.

With reference now to FIGS. 9A, an exemplary required weaving pattern is indicated including required warp-risers 971 and required warp-sinkers 973. By way of example a basket weave is shown for illustrative purposes. The weaving pattern may be converted into a reference matrix 900 as shown in FIG. 9B. The reference matrix 900 is a two dimensional array of Boolean values in which each row 901-912 corresponds to a pick. Such a pattern will produce a woven fabric having the characteristic shown in FIG. 9C.

Referring now to FIGS. 10A and 10B, a sequence of picks 951-962 is represented being added to a woven fabric. As each pick is added, it may be imaged such that the image may be compared to the corresponding row from the reference matrix 900 of FIG. 9B. Thus as the first pick 951 is added, it may be imaged and compared to the string 901 {1,1,1,0,0,1,0,1,1,0} of the first row of the corresponding first row 901 of the reference matrix 900. Similarly the second pick 952 is compared to the string 902 and so on until the whole fabric is produced. In such a manner the cloth may be inspected and graded on-loom as it is produced.

Reference is now made to the flowchart of FIG. 11 representing a possible method for detecting defects using a one-dimensional inspection analysis such as described herein. The method includes the following steps:

A reference pattern is obtained 1102, for example by referring to a pattern stored in a memory component. Additionally or alternatively, a reference pattern may be generated by on-loom learning of a repeating cycle which may then be stored in a memory for reference by a processor.

The reference pattern is converted into a reference matrix 1104, typically comprising an array of Boolean values; however, other arrays may be preferred where more complex patterns are being inspected for example using colors or the like.

An image of the fell line is obtained 1106, preferably from a photograph including all three of the shed region, the fell region and a section of woven cloth.

The image of the fell line is used to identify where along the fell-pick there is a warp-riser and where there is a warp-sinker thereby generating a characteristic sequence 1108. A digital string is generated corresponding to the characteristic sequence 1110. The digital string for the characteristic sequence is compared with the corresponding row of the reference matrix 1112. If a difference is detected 1114 then a defect may be recorded 1116 as appropriate.

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like intended to include all such new technologies a priori.

The terms "comprises", "comprising", "includes", "including", "having" and their conjugates as used herein mean "including but not limited to" and indicate that the components listed are included, but not generally to the exclusion of other components. Such terms encompass the terms "consisting of" and "consisting essentially of".

As used in this specification, the singular indefinite articles "a", "an", and the definite article "the" should be considered to include or otherwise cover both single and plural referents unless the content clearly dictates otherwise. In other words, these articles are applicable to one or more referents. For example, the term "a compound" or "at least one compound" may include a plurality of compounds, including mixtures thereof. As used in this specification, the term "or" is generally employed to include or otherwise cover "and/or" unless the content clearly dictates otherwise.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

It is appreciated that certain features of the invention, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

Although the invention has been described in conjunction with specific embodiments thereof, it is evident that other alternatives, modifications, variations and equivalents will be apparent to those skilled in the art. Accordingly, it is intended to embrace all such alternatives, modifications, variations and equivalents that fall within the spirit of the invention and the broad scope of the appended claims. Additionally, the various embodiments set forth hereinabove are described in terms of exemplary block diagrams, flow charts and other illustrations. As will be apparent to those of ordinary skill in the art, the illustrated embodiments and their various alternatives may be implemented without confinement to the illustrated examples. For example, a block diagram and the accompanying description should not be construed as mandating a particular architecture, layout or configuration.

The presence of broadening words and phrases such as "one or more," "at least," "but not limited to" or other like phrases in some instances shall not be read to mean that the narrower case is intended or required in instances where such broadening phrases may be absent.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a computer-readable medium such as a storage medium. Processors may perform the necessary tasks.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting. The scope of the disclosed subject matter is defined by the appended claims and includes both combinations and sub combinations of the various features described hereinabove as well as variations and modifications thereof, which would occur to persons skilled in the art upon reading the foregoing description.

The invention claimed is:

1. A method for inspecting woven fabric, comprising:
   providing an on-loom fabric inspection system (500);
   obtaining a reference matrix (900) representing a required weaving pattern, said reference matrix (900) comprising a two dimensional array of values arranged as a sequence of rows, each row corresponding to a series of required warp-risers (971) and required warp-sinkers (973) along a single pick;
   capturing an image of a fell-pick (805) along a fell line of the weaving area (518);
   identifying in said image a characteristic sequence of warp-risers (801) and warp-sinkers (803) along said fell-pick (805);
   generating a digital string (820) corresponding to said characteristic sequence; and
   comparing said digital string (820) with a corresponding row (901) of the reference matrix (900).

2. The method of claim 1, wherein the step of capturing said image of said fell-pick (805) further comprises:
   capturing an image of at least one section of a weaving area (518);
   transferring image data to at least one image processor (524); and
   identifying said fell-pick (805) within said image data.

3. The method of claim 2, wherein said at least one section of a weaving area (518) comprises all of a shed region (512), a woven fabric region (516) and a fell region (514).

4. The method of claim 1, wherein said digital string (820) comprises a sequence of binary or Boolean values.

5. The method of claim 1, wherein said digital string (820) comprises a sequence of values further indicating color.

6. The method of claim 1, further comprising
   providing at least one imaging device (522) configured to collect images of at least one section of a weaving area (518) of a loom;
   providing at least one image-capture trigger-mechanism (529);
   selecting a required instant during the weaving cycle; and
   said at least one image-capture trigger-mechanism (529) triggering said imaging device (522) at said required instant during the weaving cycle.

7. The method of claim 6, wherein said required instant coincides with the moment that the shed (112) is open.

8. The method of claim 1, further comprising generating an accuracy metric based upon deviations of said digital string (820) with said corresponding row (901) of the reference matrix (900).

9. The method of claim 8, wherein said accuracy metric indicates the presence of a weaving defect.

10. The method of claim 8, further comprising initiating an automatic correction process when said accuracy metric lies beyond a threshold value.

11. The method of claim 10, wherein said automatic correction process is selected from at least one of a group consisting of: stopping the loom, unweaving the cloth, adjusting battening force, producing an alert and combinations thereof.

12. The method of claim 1, further comprising generating a standard quality index for the woven fabric based upon deviations of said digital string (820) with said corresponding row (901) of the reference matrix (900).

13. The method of claim 1, wherein the step of obtaining a reference matrix (900) comprises accessing a reference pattern stored in a memory component.

14. The method of claim 1, wherein the step of obtaining a reference matrix (900) comprises:
monitoring an ongoing weaving process;
identifying a repeated cycle in said weaving process;
generating said reference matrix (900) according to said repeated cycle; and
storing said reference matrix (900) in a memory component.

15. The method of claim 1, further comprising:
providing at least one imaging device (522) configured to collect images of at least one section of a weaving area (518) of a loom; and
providing a frame grabber (532) configured and operable to receive images from said imaging device (522);
providing an image processor (524); and
sending a compact image data package (521) to said image processor (524).

16. The method of claim 15, wherein said compact image data package (521) comprises a sequence of Boolean values representing said characteristic sequence of warp-risers (801) and warp-sinkers (803) along said fell-pick (805).

17. The method of claim 15, wherein said compact image data package (521) comprises a sequence of values representing a section of a captured image including only a reduced section of the shed region (802), the fell-pick (805) and a section of the fell region (804).

18. The method of claim 1, further illuminating the shed from below.

19. The method of claim 1, further illuminating the shed from above.

20. An on-loom inspection system (500) comprising:
at least one imaging device (522) configured to collect images of at least one section of a weaving area (518) of a loom (502);
at least one image processor (524) configured and operable to detect irregularities in image data; and
at least one frame grabber (532) configured and operable to receive images of at least a fell-pick (805) from said imaging device (522) and to send a compact image data package (521) to said image processor (524);
wherein said compact image data package (521) comprises a characteristic sequence of warp-risers (801) and warp-sinkers (803) along said fell-pick (805).

21. The on-loom inspection system (500) of claim 20, further comprising at least one image-capture trigger-mechanism (529) operable to trigger said imaging device (522) to capture an image at a required instant during the weaving cycle.

* * * * *